United States Patent
Brabec et al.

(12)

(10) Patent No.: US 6,363,287 B1
(45) Date of Patent: Mar. 26, 2002

(54) STEROID ELUTION ELECTRODES LVCV, LEFT ATRIAL MEDICAL/ELECRICAL LEADS

(75) Inventors: Scott J. Brabec, Elk River; William Schindeldecker, Foreston; John L. Sommer, Coon Rapids; Douglas S. Hine, White Bear Lake, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/428,191

(22) Filed: Oct. 27, 1999

(51) Int. Cl.[7] .................................................. A61N 1/05
(52) U.S. Cl. ...................................... 607/120; 607/122
(58) Field of Search .................................. 607/120, 122

(56) References Cited

U.S. PATENT DOCUMENTS

| | | |
|---|---|---|
| 4,506,680 A | 3/1985 | Stokes |
| 4,711,251 A | 12/1987 | Stokes |
| 4,844,099 A * | 7/1989 | Skalsky et al. .............. 607/120 |
| 4,972,848 A | 11/1990 | DiDomenico et al. |
| 5,003,992 A * | 4/1991 | Holleman et al. .......... 607/120 |
| 5,433,729 A | 7/1995 | Adams et al. |
| 5,466,254 A | 11/1995 | Helland |
| 5,476,498 A | 12/1995 | Ayers |
| 5,496,360 A * | 3/1996 | Hoffmann et al. ........... 607/120 |
| 5,522,874 A | 6/1996 | Gates |
| 5,531,780 A * | 7/1996 | Vachon ........................ 607/120 |
| 5,755,765 A | 5/1998 | Hyde et al. |
| 5,755,766 A | 5/1998 | Chastain et al. |
| 5,800,495 A | 9/1998 | Machek et al. |
| 5,803,928 A | 9/1998 | Tockman et al. |
| 5,925,073 A | 7/1999 | Chastain et al. |
| 5,931,864 A | 8/1999 | Chastain et al. |
| 5,935,160 A | 8/1999 | Auricchio et al. |
| 6,198,973 B1 * | 3/2001 | Doan et al. ................. 607/120 |

OTHER PUBLICATIONS

U.S. Patent app. SN 08/895,977 filed Jul. 17, 1997 by Sommer et al for Medical Electrical Lead.

* cited by examiner

*Primary Examiner*—Carl Layno
(74) *Attorney, Agent, or Firm*—Beth L. McMahan Reed Duthler

(57) ABSTRACT

A medical electrical lead having an elongated insulative sheath carrying an elongated electrical conductor therein and having a drug-dispensing electrode assembly coupled to a distal end of the elongated conductor. The electrode assembly takes the form of a conductive electrode member having a distal electrode portion exposed exterior to the elongated sheath and a shank portion extending proximally from the distal portion and coupled to the elongated conductor. A drug release device is mounted around the shank proximal to the distal portion of the electrode member and the electrode member is provided with at least one bore extending from a surface of the release device to a surface of the distal portion of the electrode member.

10 Claims, 2 Drawing Sheets

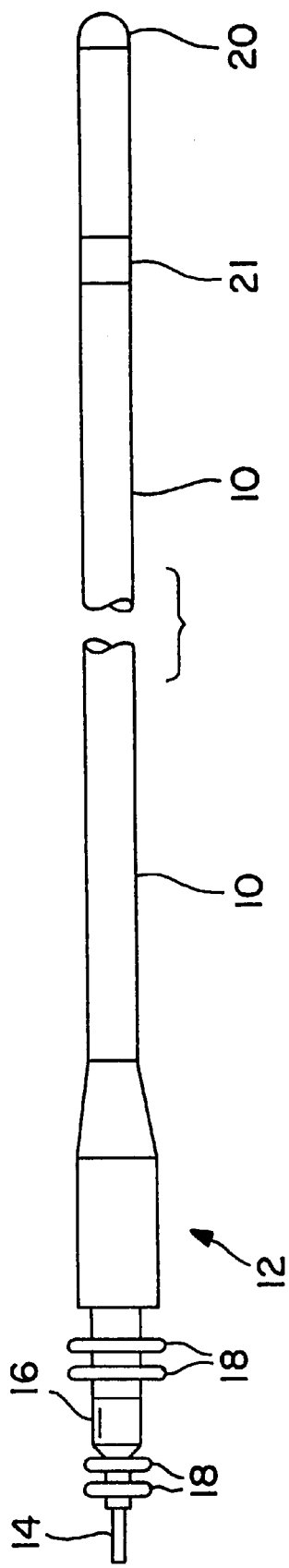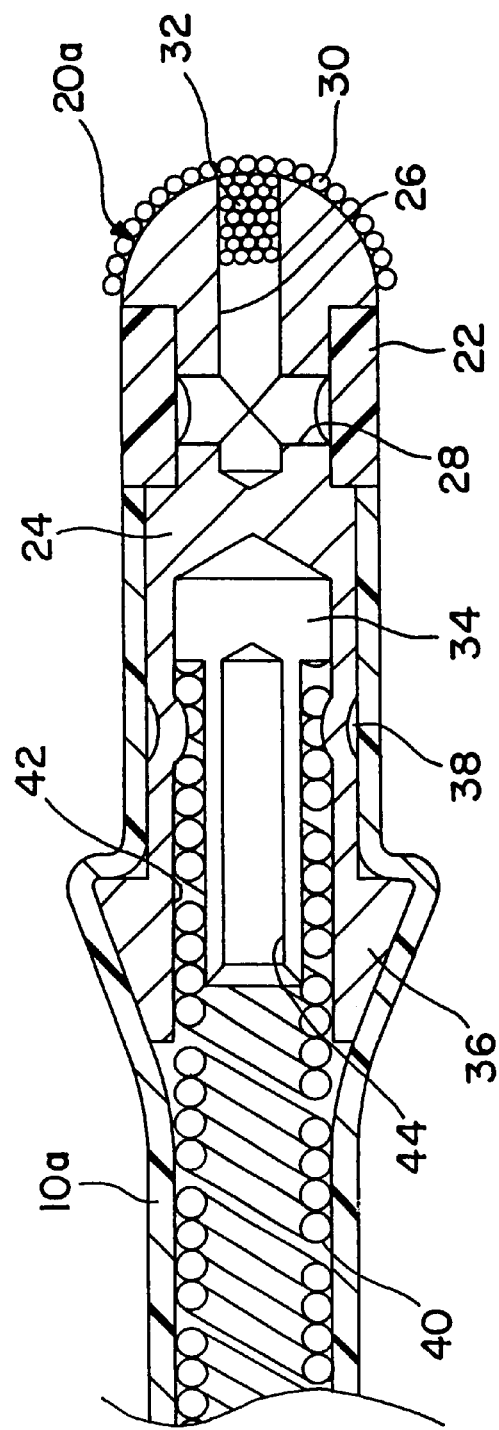

STEROID ELUTION ELECTRODES LVCV, LEFT ATRIAL MEDICAL/ELECRICAL LEADS

BACKGROUND OF THE INVENTION

Cardiac pacing leads adapted for use in the coronary sinus have been available for quite some time, for example, the Medtronic Model No. 6992 coronary sinus lead was adapted for placement in the coronary sinus and could be employed to pace the left atrium or the left ventricle, depending upon the lead was advanced into the coronary sinus. Due to the difficulty of placement of the lead in the coronary sinus and the development of leads which provided for stable fixation in the atria and ventricles, left heart pacing via the cardiac venous system was not employed to any significant degree until relatively recently. Recently, there has been a renewed interest in left side pacing, particularly in the context of bi-ventricular pacing to treat heart failure. Recent coronary sinus pacing lead designs are disclosed in U.S. Pat. No. 5,935,160 issued to Auricchio et al, U.S. Pat. No. 5,931,864 issued to Chastain et al, U.S. Pat. No. 5,925,073, also issued to Chastain et al, U.S. Pat. No. 5,803,928 issued to Tockman et al, U.S. Pat. No. 5,755,766 issued to Chastain et al, U.S. Pat. No. 5,755,765 issued to Hyde et al, U.S. Pat. No. 5,466,254 issued to Helen, U.S. Pat. No. 5,800,495 issued to Machek et al, U.S. Pat. No. 5,476,498 issued to Ayers, and U.S. Pat. No. 5,433,729, issued to Adams.

As in the case of pacing of the right heart chambers, the ability to deliver a steroid or other anti-inflammatory drug is desirable in the context of left heart pacing. Patents disclosing electrodes adapted to deliver steroid include U.S. Pat. No. 4,711,251 issued to Stokes, U.S. Pat. No. 5,522,874 issued to Gates and U.S. Pat. No. 4,972,848 issued to Di Domenico et al., all incorporated herein by reference in their entireties. In most steroid eluding leads, the steroid is adapted to be dispensed adjacent that portion of the electrode which will be located in contact with heart tissue to be stimulated. In the context of leads located in the ventricles, this has typically resulted in a lead design in which a steroid is delivered through a distally facing port or ports, extending through the distal surface of the electrode. However, it is also known to deliver steroid by means of laterally directed ports, located proximal to the distal surface of the electrode, as disclosed in the above cited '251 patent to Stokes and it is also known to deliver steroid by means of a ring shaped monolithic controlled release device located around the electrode, slightly proximal to its distal surface, as was employed in leads manufactured by Telectronics, Inc.

SUMMARY OF THE INVENTION

In the context of a lead to be implanted in the coronary vasculature, particularly after the lead has been advanced through the tortuous coronary venous system, it is often not clear which surface of the electrode which will actually be in contact with stimulatable tissue. This is particularly so in the context of a lead lacking any pre-formed bends intended to place a particular portion of the electrode in contact with stimulatable tissue. The present invention is directed toward improved drug eluting electrodes particularly adapted for use in the context of a coronary sinus lead, which are configured so that regardless of which portion of the electrode contacts stimulatable tissue, there will be an elution port for steroid or other anti-inflammatory agent located close by.

In both embodiments of the invention, the electrode includes a distal portion exposed to the exterior of the lead body and a shank extending proximal thereto, around which an MCRD containing a steroid or other anti-inflammatory drug is mounted. In one embodiment of the invention, the MCRD is coupled by means of internal channels within the electrode shank to a bore that extends to the distal surface of the electrode. In a second embodiment, the distal portion of the electrode is generally hemispherical and is provided with a shoulder that extends radially outward distal to the MCRD. The shoulder of the electrode is provided with distally directed bores extending from the distal surface of the MCRD to the surface of the distal portion of the electrode. In this second embodiment of the invention, the electrode shank includes a proximally directed internal lumen extending to the region of the shank around which the MCRD is mounted. This configuration allows for location of a stylet near the distal-most extremity of the lead, to assist in placement of the lead in a desired location in the coronary vascular system.

BRIEF DESCRIPTION OF THE DRAWINGS

FIG. 1 is a plan view of a coronary sinus lead of the type appropriate for use in conjunction with the present invention.

FIG. 2 is a cross-section through the distal portion of the lead as illustrated in FIG. 1, illustrating the structure of the first embodiment of the present invention.

DETAILED DESCRIPTION OF THE EMBODIMENT

Figure 3:
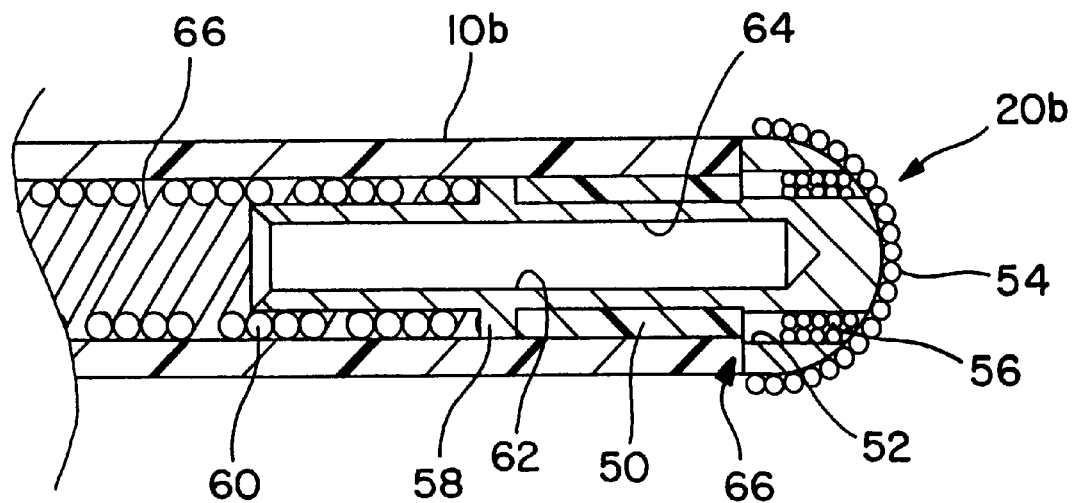
FIG. 3 is a cross-sectional view through the distal portion of a lead generally as illustrated in FIG. 1, illustrating a second embodiment of the present invention.

FIG. 1 illustrates a coronary sinus lead of a type in which the present invention may be practiced. The lead is provided with an elongated insulative sheath 10, which surrounds two mutually insulated elongated conductors. One conductor extends from a pacing electrode 20 located at the distal end of the lead to a connector pin 14 located at the proximal end of the lead. A ring electrode 21 is located proximal to the distal electrode 20 and is coupled to a second internal conductor extending through insulative sheath 10, and which is coupled to connector ring 16. Connector pin 14 and connector ring 16 are mounted to a connector assembly 12 which is intended to be inserted into the connector bore of an implantable electrical pulse generator. Sealing rings 18 are provided to seal between connector pin 14 and connector ring 16 and to seal the assembly 12 within the bore of the associated electrical pulse generator.

As illustrated, lead 10 has a generally straight configuration. However, the present invention is also believed useful in conjunction with leads having preset curvatures, for example as disclosed in U.S. Pat. No. 5,683,445 issued to Swoyer et al., and U.S. Pat. No. 6,144,882 issued to Sommer et al., both of which are incorporated herein by reference in their entireties. Lead bodies having configurations similar to others of the various patents cited above may, of course, also be substituted. However, the present invention is believed particularly valuable in the context of a lead having a generally straight lead body, adapted to be curved by means of a stylet inserted therein and thereby guided to a desired location within the coronary vasculature. Because no pre-formed curvature is set into the lead body, the surface of the electrode 20 that ultimately contacts stimulatable tissue is not predetermined.

FIG. 2 illustrates a cross-sectional view through a lead generally as illustrated in FIG. 1. The lead is provided with an outer insulative sheath 10a, corresponding generally to sheath 10 in FIG. 1 and carries a distal or tip electrode 20a, corresponding generally to electrode 20 illustrated in FIG. 1. Electrode 20a is provided with an elongated electrode shank 24, extending distally within insulative sheath 10a, and provided with an internal, proximally facing lumen 44. The distal end of coiled conductor 40 is located within lumen 44 and is coupled to the electrode shank 24 by means of a crimp core 34 and inwardly directed crimps 38. The crimp core 34 is provided with a proximally facing lumen 44, which is intended to act as a receptacle for the distal tip of an inserted stylet. The proximal end of electrode shank 24 is provided with radially extending shoulders 36 that serve to retain the insulative sheath 10a.

The distal tip of electrode 20a is generally hemispherical in configuration, and is provided with a porous sintered coating 30, corresponding to that illustrated in U.S. Pat. No. 4,506,680 issued to Stokes, incorporated herein by reference in its entirety. The electrode is also provided with a distally facing bore 32, open to the distal surface of the electrode 20a. The distal portion of bore 32 is also filled with a porous sintered structure, again corresponding to the '680 patent. A ring shaped monolithic controlled release device 22 is mounted around the electrode shank 24 in a correspondingly configured groove formed in the shank, located slightly proximal to the distal, hemispherically shaped portion of the electrode 20a. MCRD 22 may correspond to the MCRD of the above-cited Di Domenico '848 patent. One or more cross bores 28 extends through the electrode shank 24, connecting bore 26 with the interior surface of MCRD 22, whereby the steroid or other anti-inflammatory drug compounded within the MCRD 22 is eluted into the interior of the electrode and thereafter is eluted out the distal tip of the electrode through bore 26. In addition, steroid or other anti-inflammatory drug is eluted outward from the exposed surface of the MCRD 22. In this fashion, regardless of which portion of the electrode is in contact with stimulatable tissue, the electrode will elute a steroid or other anti-inflammatory drug in close proximity thereto.

FIG. 3 is a cross-section through a lead generally as illustrated in FIG. 1, illustrating a second embodiment of a lead according to the present invention. The lead is provided with an insulative outer sheath 10b, corresponding generally to insulative sheath 10 of FIG. 1. The lead is provided with an electrode 20b, corresponding generally to electrode 20 illustrated in FIG. 1. In the illustrated embodiment, electrode 20b is provided with an elongated electrode shank 64 that includes a proximally facing inner lumen 62, which serves as a receptacle for the distal tip of a stylet. A coiled conductor 66 is mounted around the proximal portion of electrode shank 64 and is welded to the electrode shank adjacent circumferentially extending shoulder 58 in order to provide for electrical and mechanical interconnection.

Located surrounding the shank 64 in a correspondingly shaped groove is a ring-shaped monolithic controlled release device 50, which may correspond to monolithic controlled release 22 discussed in FIG. 2. Rather than being exposed to the exterior of the lead, however, monolithic controlled release device 50 is surrounded by insulative sleeve 10b. The distal portion of electrode 20b is generally hemispherical, and is provided with a proximally facing circumferential shoulder 66 which extends radially outward from the electrode shank 64 and which is provided with a plurality of longitudinally extending bores 52, located therein. Bores 52 are aligned with the distal surface of monolithic controlled release device 50, and are spaced at intervals around the circumference of electrode 20b. Two, three or more such bores 52 may be provided.

The distal surface of electrode 20b is provided with a porous sintered coating 54, corresponding to that described in the above cited Stokes '680 patent, and is also provided with a porous sintered matrix 56 within each of the bores 52. In use, steroid or other anti-inflammatory drug stored within monolithic controlled release device 50 elutes through the bores 52 and out the distal portions of the bores 52. Because the bores 52 are distributed off-center and around the circumference of the electrode, regardless of the location of the electrode, delivery of steroid or other anti-inflammatory drug will occur closely adjacent that portion of the electrode in contact with stimulatable tissue. In addition, because the monolithic controlled release device is located around rather than within electrode shank 64, the proximally facing lumen 62 may extend very close to the distal tip of the electrode 20b, facilitating placement of the lead by means of a stylet.

Figure 4:
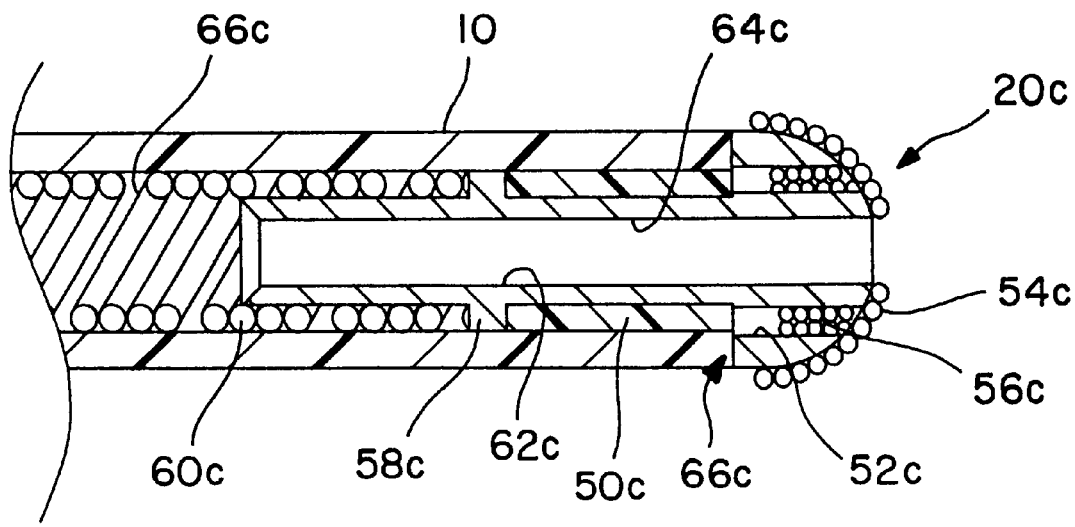
FIG. 4 is a cross-sectional view through the distal portion of a lead generally as illustrated in FIG. 1, illustrating a third embodiment of the present invention.

FIG. 4 is a cross-section through a lead generally as illustrated in FIG. 3, illustrating a third embodiment of a lead according to the present invention. Components 10c, 52c, 54c, 56c, 58c, 60c, 64c and 66c correspond to components 10b, 52, 54, 56, 58, 60, 64 and 66, respectively, of the lead as illustrated in FIG. 3. The lead differs from that illustrated in FIG. 3 in that the lumen 62c of the electrode 20c is open to the distal end of the electrode, allowing a guidewire to pass therethrough. This feature facilitates use of the lead in locations such as the coronary vasculature in which guidewire directed placement is desirable.

In conjunction with the above specification, we claim:

1. A medical electrical lead, comprising:

an elongated insulative sheath carrying an elongated electrical conductor therein; and an electrode assembly coupled to a distal end of the elongated conductor, the electrode assembly in turn comprising:

a conductive electrode member comprising a distal electrode portion exposed exterior to the elongated sheath and a shank extending proximally from the distal portion and coupled to the elongated conductor;

a release device mounted around the shank proximal to the distal portion; and wherein the electrode member is provided with at least one bore extending from a surface of the release device to a surface of the distal portion of the electrode member.

2. The lead of claim 1, wherein the distal portion comprises a radially extending shoulder located distal to the release device and wherein the bore extends from a distal surface of the release device.

3. The lead of claim 1 or claim 2, wherein the shank comprises an internal lumen opening proximally and extending distally within the shank to a region of the shank around which the release device is mounted.

4. The lead of claim 3 wherein the insulative sheath surrounds the release device.

5. The lead of claim 3 wherein the internal lumen is open to the surface of the distal portion of the electrode.

6. The lead of claim 1 or claim 2 wherein the insulative sheath surrounds the release device.

7. The lead of claim 1 wherein the at least one bore comprises a first bore extending from a distal surface of the distal portion of the electrode member to a portion of the shank around which the release device is mounted and further comprises a second bore extending from an inner surface of the release device to the first bore.

8. The lead of claim 1 or claim 2 wherein the release device is exposed exterior of the insulative sheath.

9. The lead of claim 1 or claim 2 or claim 7 wherein a porous structure is located in the at least one bore between the surface of the release device and the surface of the distal portion of the electrode member.

10. The lead of claim 1 or claim 2 or claim 7 wherein a porous structure is located on the surface of the distal portion of the electrode member.

* * * * *